United States Patent [19]

Callahan et al.

[11] 4,412,547

[45] Nov. 1, 1983

[54] NEUROLOGICAL MONITORING DEVICE

[75] Inventors: Alfred S. Callahan, Mobile, Ala.; James S. Rhodes; Timothy L. Johnson, both of Wellesley, Mass.

[73] Assignee: Neurologics, Inc., Nashville, Tenn.

[21] Appl. No.: 258,588

[22] Filed: Apr. 29, 1981

[51] Int. Cl.³ .............................................. A61B 5/04
[52] U.S. Cl. ............................................................ 128/731
[58] Field of Search .............. 128/693, 695, 696, 723, 128/731, 737

[56] References Cited

U.S. PATENT DOCUMENTS

| | | | |
|---|---|---|---|
| Re. 28,314 | 10/1974 | Maynard | 128/731 |
| 2,760,105 | 8/1956 | Michaels | 128/731 |
| 3,185,925 | 5/1965 | Grass | 128/731 |
| 3,222,598 | 12/1965 | Pollard | 128/731 |
| 3,413,546 | 11/1968 | Riehl et al. | 128/731 |
| 3,498,287 | 3/1975 | Ertl | 128/731 |
| 3,696,808 | 10/1972 | Roy et al. | 128/731 |
| 3,699,947 | 10/1972 | Maynard | 128/731 |
| 3,841,309 | 10/1974 | Salter et al. | 128/731 |
| 3,892,227 | 7/1975 | Coursin et al. | 128/731 |
| 3,893,450 | 7/1975 | Ertl | 128/731 |
| 3,901,215 | 8/1975 | John | 128/731 |
| 3,910,258 | 10/1975 | Pisarski et al. | 128/731 |
| 4,031,883 | 6/1977 | Fehmi et al. | 128/731 |
| 4,037,586 | 7/1977 | Grichnik | 128/731 |
| 4,155,352 | 5/1979 | Toglia et al. | 128/733 |
| 4,170,225 | 10/1979 | Criglar et al. | 128/732 |
| 4,188,956 | 2/1980 | John | 128/731 |
| 4,213,465 | 7/1980 | Renheim | 128/731 |
| 4,214,591 | 7/1980 | Sato et al. | 128/731 |
| 4,215,697 | 8/1980 | Demetrescu | 128/731 |

FOREIGN PATENT DOCUMENTS

| 1247491 | 10/1968 | United Kingdom | 128/731 |
|---|---|---|---|
| 1247492 | 9/1971 | United Kingdom | 128/731 |

Primary Examiner—William E. Kamm
Attorney, Agent, or Firm—Davis, Hoxie Faithfull & Hapgood

[57] ABSTRACT

A brain wave monitoring device for monitoring brain wave activity measures the frequency and amplitude of brain wave signals from the left and right hemispheres of the brain. The brain wave signals are filtered and applied to an amplitude detecting device, and a frequency-to-voltage converter which employs a zero-crossing technique such that signal frequencies are detected independent of signal magnitude. The amplitude and frequency information is displayed on separate power and frequency displays on the front panel of the brain wave monitoring device. Each of the power and frequency displays employ a pair of linear LED arrays such that a "bar graph" of the amplitude and frequency of the brain waves is produced. Additionally, signals indicative of the power of the brain waves on the left and right hemispheres are selectively applied to a voltage controlled oscillator having an earphone output, such that the operator may listen for differences in amplitude between left and right hemisphere brain waves.

7 Claims, 6 Drawing Figures

NEUROLOGICAL MONITORING DEVICE

The present invention is directed to a neurological monitoring device for monitoring brain wave activity. The present invention is related to the subject matter of co-pending U.S. patent application Ser. No. 258,587, by Callahan, Rhodes, Johnson and Durden, for "Neurological Monitoring Device Test Circuitry," filed Apr. 29, 1981. Specifically, the test circuitry disclosed in the co-pending application is adapted to be used with the neurological monitoring device of the present invention, and is thus set forth in the description of the present invention for the sake of completeness.

DESCRIPTION OF THE INVENTION

Electroencephalographs (EEG's) display and record voltage potentials produced by the brain. These voltages are developed by applying electrodes to the scalp of a patient, and by applying the outputs of the electrodes to an amplifying and recording apparatus, a record of the brain waves may be produced. The brain wave voltages are very small, on the order of 50 microvolts, and the degree of amplification required to produce a discernable record is therefore high.

The brain wave voltage potentials vary in amplitude and frequency. For example, "alpha" waves have a voltage of approximately 50 microvolts and have a frequency which varies around 9–10 cycles per second. The alpha waves are typically found in the occipital area of the scalp. "Beta" waves on the other hand, occur mainly over the frontal and temporal lobes and are of even lower voltage and higher frequency than the alpha waves. In addition, certain other waves may be found in normal subjects.

The usefulness of electroencephalograph monitoring during operations is well known. By monitoring the patient's brain waves during an operation, the patient's physical state may be determined by proper interpretation of the EEG. EEG monitoring is presently recommended for cerebrovascular surgery, cardiopulmonary by-pass and deliberate hypotension, and as a measure of anasthetic depth.

The signals from the EEG are of a highly complex nature, since a variety of signals such as alpha waves, beta waves, and the like are produced, each being very low in amplitude, and varying rapidly with time. Rapid interpretation of the signals is therefore extremely difficult. Various techniques have been proposed in order to overcome this problem, many of which produce a printed record of the relative magnitudes of selected frequency components of the waveform. However, appreciable time and operator experience is still required for this type of EEG output. Thus, practical considerations such as the size and complexity of the EEG monitoring equipment, the need for a highly skilled technician to run it, and the difficulty in making rapid intraoperative interpretations of the EEG have limited its popularity as an intraoperative monitor.

Recent advances in electronic technology, such as automated EEG monitoring, have reduced the magnitude of some of these problems. Although automated EEG processing techniques do not improve the sensitivity of the EEG, the automated techniques are much simpler to use and provide a clearer display of relevant information. However, many of the automated techniques require the use of expensive equipment such as a dedicated mini or microcomputer. In fact, techniques such as multiple differential analysis, period-amplitude analysis, and augmented delta quotient analysis all require expensive special purpose electronic equipment which is not generally available.

Still other special purpose electronic devices have been provided to produce highly specific indications of one or several of the characteristics of brain wave signals. For example, U.S. Pat. No. 3,696,808 to Roy et al. provides for the simultaneous alphanumeric readout of brain wave signals at a particular frequency from the two hemispheres of the brain. However, the Roy device cannot simultaneously produce information over more than the single chosen frequency at any one time. Further, the technician is required to monitor the alphanumeric readout at a variety of locations on the display, thereby making rapid decisions more difficult.

Another example of a highly specific EEG monitoring device is taught by U.S. Pat. No. 3,222,598 to Pollard. The Pollard circuitry extracts the alpha wave to the exclusion of all other frequencies and converts the frequency thereof to a voltage. This alpha wave frequency information is provided as a voltage display or record. Like Roy et al., the Pollard device requires the visual inspection of the output thereof by a trained technician in order to extract the information. Further, Pollard merely provides a single channel analyzer whereby a unilateral hemisphere dysfunction, which requires the comparison of one hemisphere to the other, cannot be detected. Clearly, rapid derivation of frequency information and amplitude information for both the left hemisphere and right hemisphere under real time conditions is made extremely difficult by the amount of information which need be considered.

Further, the Roy and Pollard devices are typical of prior art systems since they are frequency selective and provide no quantitative information relating to what the frequency of the signal of interest, such as the alpha wave, is. That is, they are designed to choose a particular frequency for further processing, and once chosen, the information contained in other frequencies is disregarded. Thus, in the event that the frequency of the signal of interest changes, the operator must accordingly search for the new frequency, and may not even be aware that a new frequency for the signal of interest exists. Since it has been found that the frequencies of the brain waves are time dependent and change during the course of an operation, these prior art devices are therefore severely limited in their ability to respond to the brain signals in the proper manner.

It is therefore an object of the present invention to overcome the difficulties encountered in the prior art EEG devices.

It is a further object of the present invention to provide a brain wave monitoring device which provides brain wave information throughout a wide frequency range and which uses an extremely simple circuitry arrangement in order to accomplish this objective.

It is a further object of the present invention to provide a brain wave monitoring device for providing an extremely simple brain wave display from which rapid interpretations of brain wave signals can be made.

It is a further object of the present invention to provide a brain wave monitoring device which may be more accurately and easily operated for any given level of operator skill and training.

It is a further object of the present invention to provide a brain wave monitoring device which can simultaneously provide amplitude and frequency information from both hemispheres of the brain in order to monitor unilateral hemisphere brain dysfunction in real time.

In accordance with the first aspect of the present invention, a device is provided for monitoring brain waves produced by a pair of electrodes respectively placed on the left and right hemispheres of a patient's head. The device comprises left and right analyzing means each receiving the brain waves from an associated one of the pair of electrodes, each of the left and right analyzing means providing brain wave amplitude and frequency information from the left and right hemispheres, respectively. A brain wave amplitude display having first and second linear arrays disposed side-by-side receive and display the brain wave amplitude information from the left and right hemispheres respectively. A brain wave frequency display having first and second linear arrays disposed side-by-side receive and display the brain wave frequency information from the left and right hemispheres, respectively. Finally, an audible brain wave amplitude indicator selectively receives the brain wave amplitude information from one of the left and right hemispheres by way of a switch, the audible brain wave amplitude indicator converting the brain wave amplitude information into an audio signal having a frequency proportional to the amplitude of the brain wave.

The left and right analyzing means in accordance with this aspect of the present invention each comprise a filter for receiving the brain waves and having a predetermined pass band. A detector receives the output of the filter for detecting the amplitude of the brain waves for providing the brain wave amplitude information. Finally, a converter receives the output of the filter and detects, over a frequency range greater than the predetermined pass band, the frequency of the brain waves having amplitudes above a predetermined amplitude, to thereby allow the frequency of the brain wave to be tracked over the greater frequency range.

In accordance with a second aspect of the present invention, a brain wave analyzer adapted to receive a brain wave signal, analyze the brain wave signal, and provide outputs indicating the frequency and amplitude characteristics of the brain wave signal is provided. The brain wave analyzer comprises a filter for receiving the brain wave signal and having a predetermined pass band. A detector receives the output of the filter and detects the amplitude of the brain wave signal. Finally, a converter also receives the output of the filter and detects over a frequency range greater than the predetermined pass band, the frequency of the brain wave signals having amplitudes above a predetermined amplitude, to thereby allow the frequency of the brain wave signal to be tracked over the greater frequency range.

In accordance with the first and second aspects of the invention, the converter includes a device for selecting only those brain wave signals having amplitudes above the predetermined amplitude, a zero crossing detector receiving an output from the selector device, and a frequency-to-voltage converter receiving the output of the zero crossing detector for providing a voltage proportional to the frequency of the zero crossing output.

These and other objects of the invention will be described with reference to the following drawing figures of which:

Figure 6:
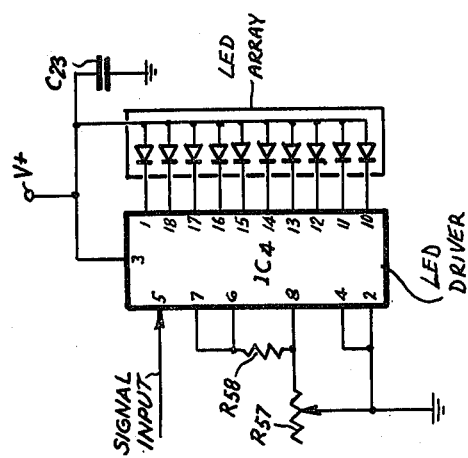
Figure 5:
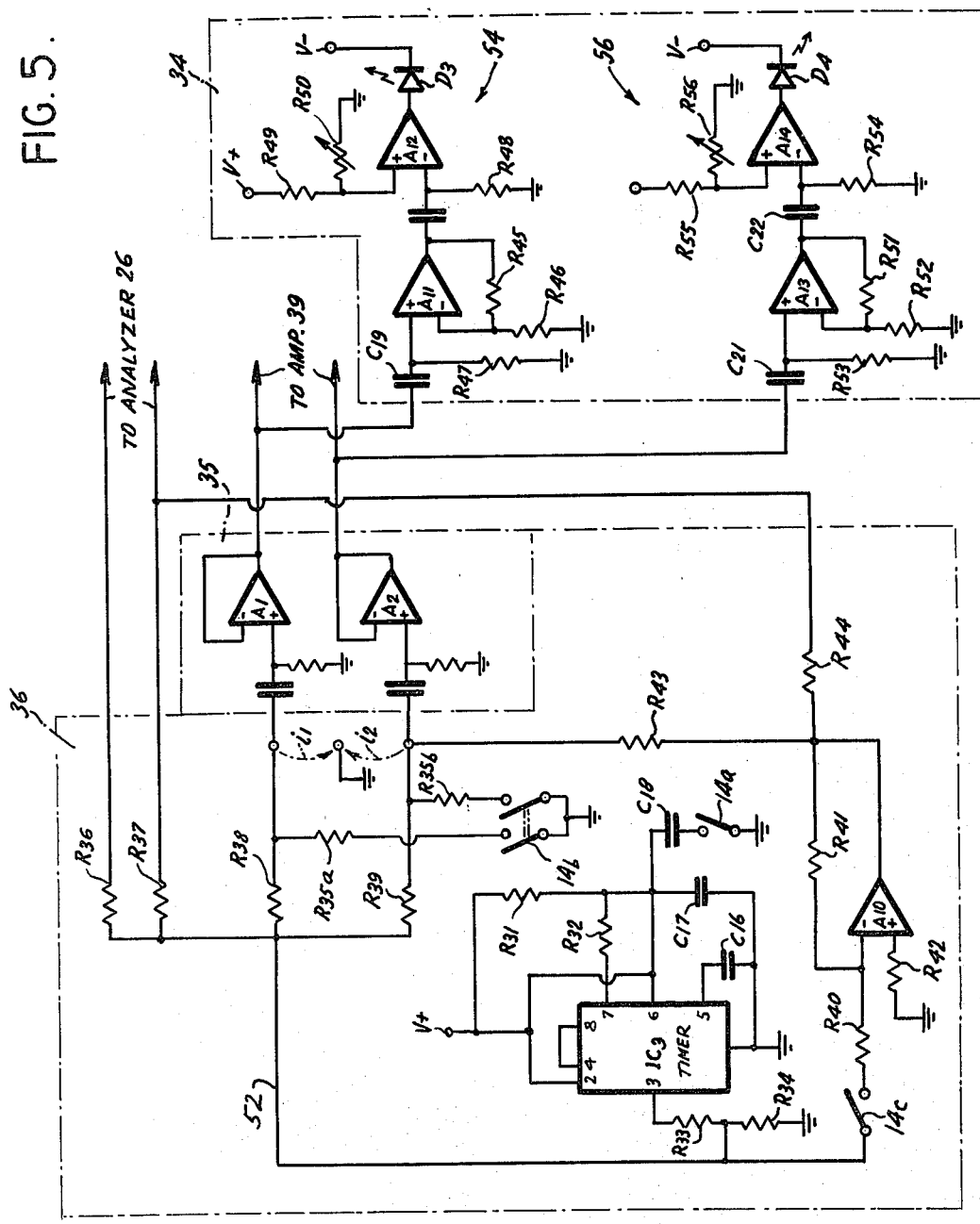

FIG. 5 is a schematic diagram illustrating the circuitry, in accordance with the above-cited co-pending application Ser. No. 258,587, which tests the impedance of the current paths through the patient's head during the monitoring of the brain waves, and associated circuitry for providing a self-test of the brain wave monitoring device in order to determine whether the device is functioning properly; and FIG. 6 is a schematic diagram illustrating the circuit arrangement for driving the LED displays employed in the brain wave monitoring device in accordance with the present invention.

Figure 1:
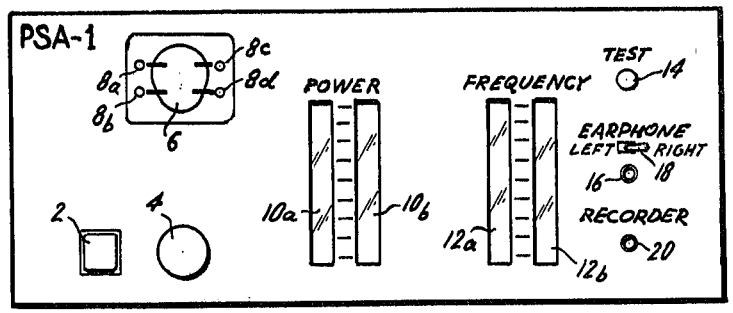
FIG. 1 is a front view of the brain wave monitoring device in accordance with the present invention.

FIG. 1 is an illustration of the front panel of the brain wave monitoring device in accordance with the present invention. ON/OFF switch 2 and potentiometer control 4 are disposed in the lower left hand corner of the panel. In the upper left hand corner is a diagram 6 of the patient's head illustrating the placement of the bipolar electrodes. Associated with diagram 6 are four LED indicators 8a–8d, which are used to determine the impedance properties of the current paths in the patient. To the right of diagram 6 is the brain wave power indicator comprising a pair of vertically disposed linear LED arrays 10a and 10b arranged side-by-side. To the right of the power indicators are frequency indicators comprising a similar pair of vertically disposed linear LED arrays 12a and 12b also arranged side-by-side. A push button test switch 14, earphone output jack 16 and associated toggle switch 18, and recorder output jack 20 are provided on the right hand portion of the front panel.

Figure 2:
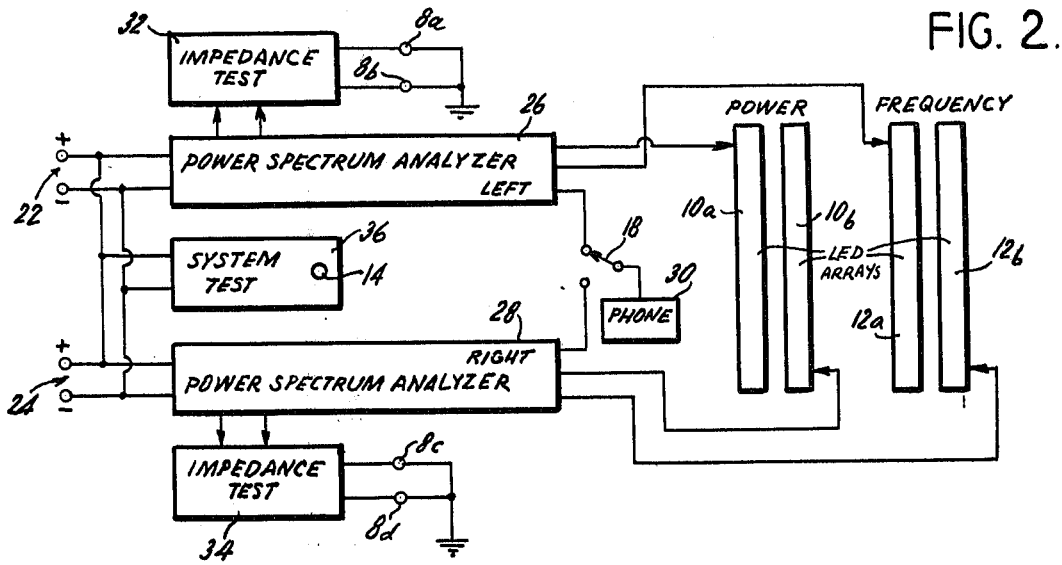
FIG. 2 is a block diagram illustrating the overall system organization in the brain wave monitoring device in accordance with the present invention.

FIG. 2 is a block diagram of the system organization of the brainwave monitoring device in accordance with the invention. Bipolar inputs 22 and 24 from the electrodes placed on the left and right portions of the patient's head are applied to left and right Power Spectrum Analyzers 26 and 28, respectively. The outputs from Power Spectrum Analyzer 26 are applied to power LED display 10a and frequency LED display 12a, while the outputs from Power Spectrum Analyzer 28 are applied to power LED display 10b and frequency LED display 12b. Headphone circuitry 30 receives a signal from one of Power Spectrum Analyzers 26 and 28 via toggle switch 18. System test circuit 36, having test button 14, is connected to the bipolar inputs 22 and 24 of analyzers 26 and 28, respectively. Finally, Power Spectrum Analyzers 26 and 28 provide signals to impedance test circuits 32 and 34, respectively. Impedance test circuit 32 provides an output to LED indicators 8a and 8b, while impedance test circuit 34 provides signals to LED indicators 8c and 8d.

Figure 3:
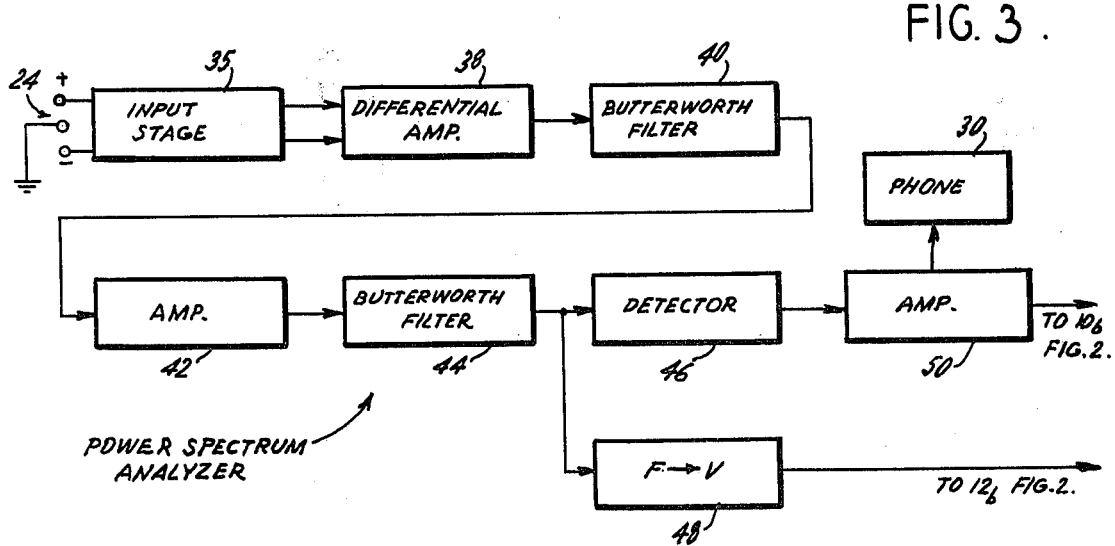
FIG. 3 is a block diagram illustrating the contents of a single Power Spectrum Analyzer used in accordance with the brain wave monitoring device of FIG. 2.

The contents of Power Spectrum Analyzer 28 will be discussed in more detail with reference to FIG. 3. The details of Analyzer 26 are identical to that of Analyzer 28 and have therefore been omitted. The bipolar inputs 24 are applied to input stage 35 which functions to filter the signals and provide a high input impedance path therefor. The bipolar outputs of stage 35 are applied to differential amplifier 38 which also functions to filter the signals input thereto and provides a differential amplification of the bipolar signals to produce a single output signal. This output signal is applied to Butterworth filter 40, the output of which is applied to a second Butterworth filter 44 via amplifier 42. Butterworth filters 40 and 44 function to provide the appropriate pass band for the system. The output of filter 44 is applied on the one hand to detector 46 and on the other hand to a frequency-to-voltage converter 48, the output of the latter being applied to frequency display 12b, FIG. 2. The output of detector 46 is applied on the one hand to earphone circuitry 30 and on the other hand to amplifier 50, the output of amplifier 50 being applied to the power display 10b, FIG. 2.

Figure 4:
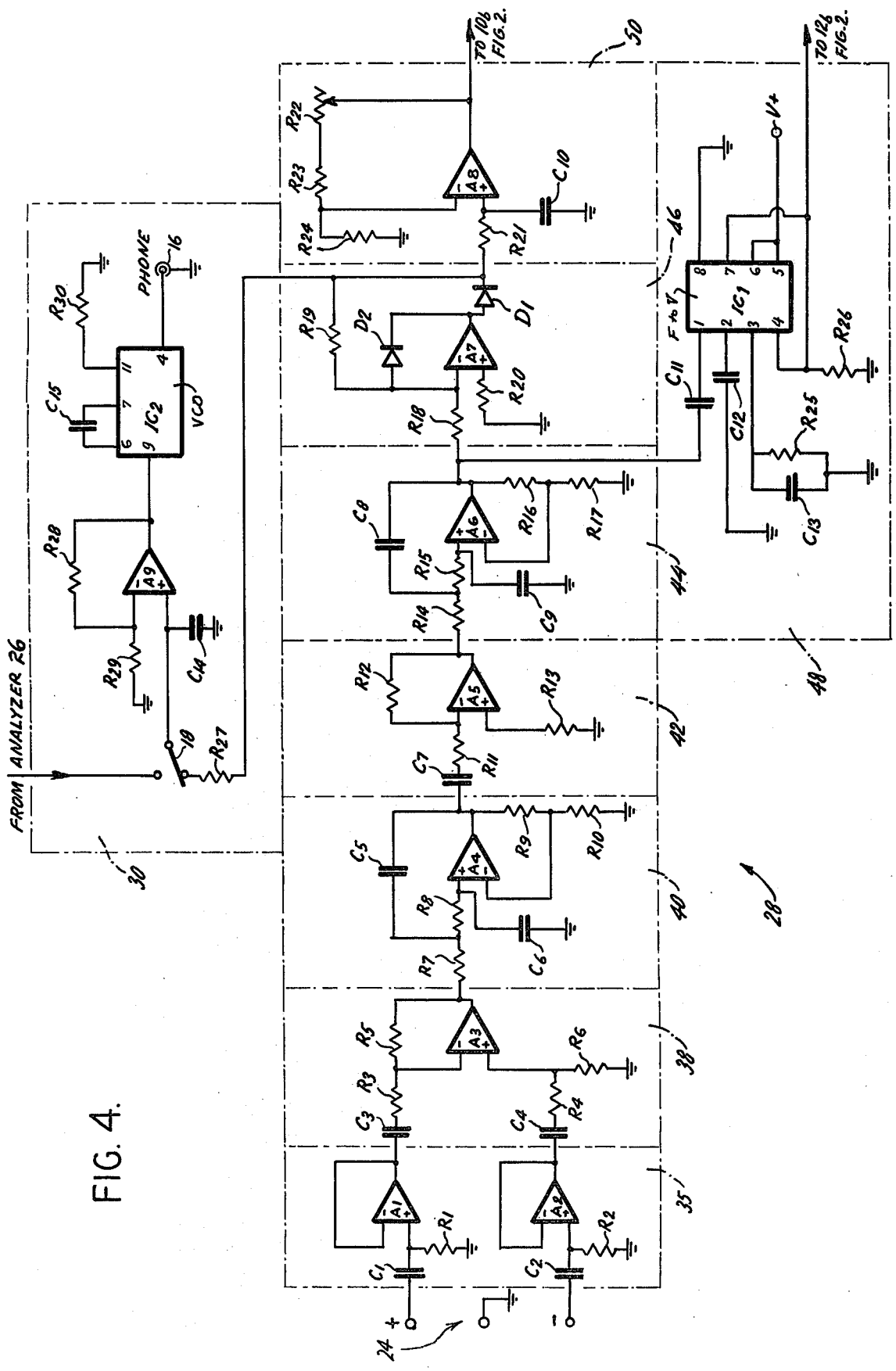
FIG. 4 is a schematic diagram illustrating the circuitry contained in the Power Spectrum Analyzer employed in the brain wave monitoring device in accordance with the present invention.

The contents of each of the blocks illustrated in FIG. 3 will be discussed with reference to FIG. 4. Again, the details of Analyzer 26 are identical to those of Analyzer 28 and have therefore been omitted. The bipolar input from the electrode is applied to input stage 35 comprising a pair of high pass filters C1/R1 and C2/R2 and operational amplifiers A1 and A2. Specifically, the positive bipolar terminal is applied to the noninverting input of amplifier A1 via capacitor C1, the output of amplifier A1 being fed back to the inverting input thereof. Similarly, the negative terminal of the electrode is applied to the noninverting input of amplifier A2 via capacitor C2, the output thereof being fed back to the inverting input. The noninverting inputs of amplifiers A1 and A2 are applied to ground via resistors R1 and R2, respectively.

The outputs of amplifiers A1 and A2 are delivered to differential amplifier stage 38 which comprises a pair of high pass filters C3/R3, and C4/R4, and a differential amplifier A3. Specifically, the output of amplifier A1 is delivered to the inverting input of amplifier A3 via filter C3/R3, while the output of amplifier A2 is delivered to the noninverting input of amplifier A3 via filter C4/R4. The output of amplifier A3 is fed back to the inverting input thereof via resistor R5, while the noninverting input of amplifier A3 is fed to ground via resistor R6.

The output of differential amplifier stage 38 is applied to Butterworth filter 40 which comprises operational amplifier A4, resistors R7–R10, and capacitors C5 and C6. The output of amplifier A3 is applied to the noninverting input of amplifier A4 via resistors R7 and R8. The output of amplifier A4 is fed back to the node common to resistors R7 and R8 via capacitor C5, the output of amplifier of A4 also being fed back to the inverting input thereof via resistor R9. The noninverting and inverting inputs to amplifier A4 are applied to ground via capacitor C6 and resistor R10, respectively.

The output of the Butterworth filter taken at the output of amplifier A4 is delivered to amplifier stage 42 which comprises operational amplifier A5, resistors R11–R13 and capacitor C7. The output of the Butterworth filter is applied to the inverting input of amplifier A5 via capacitor C7 and resistor R11, the output of amplifier A5 being fed back to its inverting input via resistor R12. The noninverting input to amplifier A5 is applied to ground via resistor R13.

The output of amplifier A5 is delivered to the second Butterworth filter 44 which is substantially identical to Butterworth filter 40, resistors R14–R17 corresponding to resistors R7–R10, respectively, capacitors C8 and C9 corresponding to capacitors C5 and C6, respectively. Amplifiers A6 and A4 are substantially identical. The output of Butterworth filter 44 is applied to detector stage 46 and converter stage 48.

Detector stage 46 comprises operational amplifier A7, resistors R18–R20 and diodes D1 and D2. The output of Butterworth filter 44 is applied to the inverting input of amplifier A7 via resistor R18. The output of amplifier A7 is connected to cathode of diode D2, the anode of diode D2 being applied to the inverting input of amplifier A7. The output of amplifier A7 is also applied to the anode of diode D1, the cathode of diode D1 being applied to the inverting input of amplifier A7 via resistor R19. The noninverting input of amplifier A7 is applied to ground via resistor R20. The output of detector 46 is applied on the one hand to amplifier stage 50 and on the other hand to earphone circuitry 30.

Amplifier stage 50 comprises operational amplifier A8, resistors R21–R24 and capacitor C10. The output of detector 46 taken from the cathode of diode D1 is applied to the noninverting input of amplifier A8 via resistor R21. The output of amplifier A8 is fed back to the inverting input thereof via the wiper of variable resistor 22 and resistor R23. The inverting and noninverting inputs of amplifier A8 are applied to ground via resistor R24 and capacitor C10, respectively. The output from operational amplifier A8 is applied to the power LED display 10b, FIG. 2.

The output of amplifier A6 in Butterworth filter 44 is applied to the frequency-to-voltage conversion device 48 which comprises integrated circuit IC1, resistors R25, R26 and capacitors C11–C13. IC1 may be a National Semiconductor LM2907 Frequency-to-Voltage Converter. Pin 1 of IC1 receives the output of amplifier A6 via capacitor C11. Pin 2 of IC1 is applied to ground via capacitor C12. Pin 3 of IC1 is applied to ground via resistor R25 and capacitor C13 connected in parallel. Pins 4 and 7 are tied together and provide the input signal to the frequency LED display 12b, FIG. 2. Pins 4 and 7 are also applied to ground via resistor R26. The positive supply voltage is applied to pins 5 and 6, and pin 8 is applied directly to ground.

The output of detector 46 taken at the cathode of diode D1 is applied to earphone circuitry 30 which comprises operational amplifier A9, integrated circuit IC2, resistors R27–R30, capacitors C14, C15, switch 18, and earphone jack 16. The output of detector 46 is applied to the noninverting input of amplifier A9 via resistor R27 and switch 18. The output of amplifier A9 is fed back to the inverting input thereof via resistor R28. The inverting and noninverting inputs of amplifier A9 are applied to ground via resistor R29 and capacitor C14, respectively. The output of amplifier A9 is applied to a voltage controlled oscillator which is included in IC2, a CD4046 Phase-Locked Loop. The signal from amplifier A9 is connected to pin 9 of integrated circuit IC2. Pins 6 and 7 of IC2 are connected to each other via capacitor C15, pin 11 of IC2 being applied to ground via resistor 30. Finally, pin 4 of IC2 is applied to ground through earphone jack 16.

The Power Spectrum Analyzer circuitry illustrated in FIG. 4 operates as follows. The bipolar signal at input 24 is applied to input stage amplifiers A1 and A2 which provide a very high impedance, on the order of $10^{12}$ ohms, in order to isolate the circuitry from the patient. The high pass filters comprising resistor/capacitor pairs R1/C1, R2/C2, R3/C3, R4/C4, and R11/C7, are designed to have a low frequency cutoff at approximately 2–4 Hz. The outputs of amplifiers A1 and A2 are applied to amplifier A3 which functions as a differential preamp having a gain of approximately 1000. The amplified output from amplifier A3 is applied to second order Butterworth filter 40, the components of which are designed to provide a rapid roll-off in frequency response above 12 Hz. The output from Butterworth filter 40 is applied to amplifier A5 which functions to amplify the signal input thereto by approximately 82. The output of amplifier A5 is applied to second order Butterworth filter 44 having characteristics substantially identical to that of Butterworth filter 40. Thus, the signal available at the output of amplifier A6 represents the filtered and amplified differential signal produced by the bipolar electrode 24. The filters combine to produce lower and upper filter skirts at around 4 and 12 Hz, respectively. However, signals having frequencies above and below the pass band, although attenuated, will still exist to some degree. As will be discussed in more detail below, the frequency detection is based on zero crossings of the signals and is thus independent of amplitude. Therefore, a band of signal frequencies broader than the filter pass band may be examined for spectral content.

The output from amplifier A6 is level detected in detector 46 which serves to half-wave rectify the signal input thereto. The output of detector 46 is applied to amplifier stage 50 which provides an adjustable gain for the power LED display 10b, variable resistor R22 corresponding to control knob 4, FIG. 1. By adjusting resistor R22 the LED response may be adjusted as desired. The LED display provides a simple indication of the power of the brain waves.

The output of amplifier A6 is also applied to frequency-to-voltage converter 48 which comprises IC1 and associated circuitry. IC1 provides three functions. Recalling that frequencies over a broad band will be applied to the converter 48 (the frequencies outside the pass band being attenuated), it is necessary to eliminate minute system noise signals so that they do not affect the brain wave indications. This is accomplished in IC1 with a Schmidt trigger device having a preset hysteresis which provides a threshold voltage swing through which the signal must pass in order for it to be analyzed further. In this manner, the system may be easily adjusted to respond to signals of any frequency at or above a given amplitude. The output of the Schmidt trigger is applied to a zero crossing detector which functions to provide an output signal whenever the Schmidt trigger changes state. Finally, this zero crossing signal is applied to a frequency-to-voltage converter, the frequency-to-voltage converter producing a voltage proportional to the frequency of the zero crossing signals. Converter 48 can thus provide the frequency information over a broad range of frequencies (on the order of 0–20 Hz) to frequency LED display 12b, FIG. 2.

The output of detector 46 is applied to earphone circuitry 30 comprising amplifier A9, integrated circuit IC2, and associated circuitry. The detected power signal is suitably amplified in amplifier A9 and delivered to the voltage controlled oscillator input at pin 9 of IC2. The voltage applied to pin 9 of IC2 is proportional to the amplitude of the detected signal. The voltage controlled oscillator in IC2 functions to convert this voltage to an audio frequency proportional to the voltage. The frequency signal which is taken from pin 4 of IC2 is applied to earphone jack 16. Thus, by listening to the frequency of the signal available at the earphone jack, and by selecting the left or right hemisphere of the brain, the operator can listen to any tonal differences between the left and right hemispheres, to thereby alert the operator to any differences in brain wave signal power between the left and right hemispheres of the brain.

Thus, the dual channel monitoring device in accordance with the present invention provides the following major advances over the prior art techniques of monitoring brain waves. The first is a rapid and simple indication of brain dysfunction. The signal power level as indicated in the output from side-by-side linear LED displays 10a and 10b, and the signal frequencies as indicated in the output of side-by-side linear LED displays 12a and 12b may readily be monitored for absolute response, since the output is in the form of a "bar graph" which does not require the operator to read and interpret an alphanumeric display or chart record. Further, the operator can quickly and easily determine the existence of any type of unilateral hemisphere dysfunction since such dysfunction will produce a visible difference between the outputs of power displays 10a and 10b and/or frequency displays 12a and 12b. The detection of unilateral hemisphere dysfunction is further enhanced by providing an audible indication of signal power from earphone jack. By switching back and forth using switch 18, the operator can readily detect differences in hemisphere response.

Still further, the present invention is advanced over the prior art devices since it provides an indication of, and tracks the frequency of the signal of interest over a broad range of frequencies. The operator can therefore monitor both amplitude and frequency without having to know or select a priori the frequency of interest to the exclusion of other frequencies. This is accomplished using a minimal amount of additional circuitry and provides the capability of monitoring the patient's condition throughout a wide range of operative procedures without further adjustment by the operator.

FIG. 5 is a schmatic illustration of system test circuit 36 and impedance test circuit 34, connected to the Power Spectrum Analyzer 28, FIG. 2. System test circuit 36 comprises integrated circuit IC3 and associated circuitry comprising resistors R31–R44 and capacitors C16–C18. IC3 is a timing device such as the LM555 timer and provides a pulsating DC signal having predetermined amplitude and frequency characteristics on signal output line 52. Pins 4 and 8 of IC3 are directly applied to the supply voltage, while pin 7 receives the supply voltage via resistors R31 and R32. Pin 6 and pin 2 receive the supply voltage via resistor R31. Pin 5 is connected to pin 6 via capacitors C16 and C17. Pin 1 is directly applied to ground, and is connected to pin 5 via capacitor C16. Pin 6 is applied to switch 14a via capacitor C18. The signal output from IC3 taken from pin 3 is applied to signal output line 52 via resistor R33, and is applied to ground via resistors R33 and R34. The output signal on line 52 is applied to left and right Power Spectrum Analyzer channels 26 and 28 via resistors R36/R37 and R38/R39, respectively, at the bipolar inputs 22 and 24, respectively, resistors R38 and R39 being connected to the noninverting inputs to amplifiers A1 and A2, respectively. The noninverting inputs to amplifiers A1 and A2 are applied to ground via resistors R35 and R35b, respectively, in series with double pole switch 14b. In FIG. 5, the input stage 35 for Power Spectrum Analyzer 28 is shown in detail, the application of the signal to Power Spectrum Analyzer 26 being identical to that for Power Spectrum Analyzer 28.

The output signal on line 52 is applied to the inverting input of amplifier A10 via switch 14c and resistor R40.

The output of amplifier A10 is fed back to the inverting input thereof via resistor R41, the noninverting input of amplifier A10 being applied to ground via resistor R42. The output of amplifier A10 is further applied to the input terminal connected to input stage amplifier A2 via resistor R43, the same input terminal to amplifier A2 receiving the signal on line 52 via resistor R39. In an identical manner, the output of amplifier A10 is also applied to the input stage of Analyzer 26 via resistor R44.

Impedance test circuitry 34 for Power Spectrum Analyzer 28 is also illustrated in detail in FIG. 5. The details of impedance test circuitry 32 for Power Spectrum Analyzer 26 is identical to that shown in FIG. 5 and has therefore been omitted. Respective outputs from amplifiers A1 and A2 are applied to a pair of identical comparator circuits 54 and 56. Comparator circuit 54 includes an amplifier A11 which receives at its noninverting input the output from input stage amplifier A1 via capacitor C19. The output of amplifier A11 is fed back to the inverting input thereof via resistor R45. The inverting and noninverting inputs to amplifier A11 are applied to ground via resistors R46 and R47, respectively. The output of amplifier A11 is applied to the inverting input of amplifier A12 via capacitor C20, the output of amplifier A12 being applied to the anode of LED D3, the cathode of which is connected to a negative supply voltage. The inverting input to amplifier A12 is applied to ground via resistor R48, the noninverting input being applied to the positive supply voltage via resistor R49 on the one hand and being applied to ground via variable resistor R50 on the other hand. The comparator circuit 56 is identical to circuit 54, capacitors C21, C22 corresponding to capacitor C19 and C20, amplifiers A13, A14 corresponding to amplifiers A11, A12, resistors R51-R56 corresponding to resistors R45-R50 and diode D4 corresponding to diode D3, respectively.

Operation of the system test circuitry 36 and impedance test circuitry 34 will now be discussed. IC3 and associated circuitry produce a pulsed (square wave) DC output at about 23-24 millivolts on signal line 52, the frequency of the output being either 120-150 Hz when switches 14a and 14c are open, or about 9 Hz when switches 14a and 14c are closed. Switches 14a-14c are controlled in unison, switches 14a and 14c embodied in a quad analog switch such as the CD4016, switch 14b being embodied in a low resistance analog switch such as the CD4066. Assuming that switches 14a-14c are open, the 120-150 Hz signal is applied to the input terminals 24 of input stage 35 via resistors R38 and R39. As shown in FIG. 5, current paths $i_1$ and $i_2$ will be established from each of the bipolar electrodes to the ground electrode. Thus, as the impedance through paths $i_1$ and $i_2$ is decreased, the amplitude of the signal applied to the input stage 35 will be decreased, while as the impedance of the paths $i_1$ and $i_2$ increases, the amplitude of the signal applied to the input stage 35 accordingly increases. The signal output from stage 35 is applied to the comparator circuits 54 and 56, where they are subject to amplification in amplifiers A11 and A13, respectively, and are compared with a reference level at amplifiers A12 and A14, respectively. If the signals applied to the inverting inputs of amplifiers A12 or A14 are of sufficient magnitude, indicating that the impedance along paths $i_1$ or $i_2$ is above a predetermined level (typically 5K ohms), the outputs of amplifiers A12 or A14 will be drawn negative to thereby turn the associated diode D3 or D4 off to indicate that one of the respective paths $i_1$ or $i_2$ presents an impedance which is prohibitively high. The impedance test signal may be applied during monitoring since the 120-150 Hz signal is far outside the pass band provided by the Butterworth filters, and since any brain wave signals (around 50 uV) present at the inputs to stage 35 will have a negligible effect on the 23-24 mV impedance signal.

The system test circuitry 36 further provides for the injection of a signal having known frequency and amplitude characteristics into the left and right Power Spectrum Analyzers 26 and 28 so that the operator may readily determine whether the associated circuitry is operating properly by simply pushing a button. When pushbutton 14 is activated by the operator, switches 14a-14c, FIG. 5 are closed. Closure of switch 14a adds capacitor C18 into the timer circuit of IC3 to thereby provide a signal on line 52 of approximately 23-24 mV at 9 Hz, the approximate frequency of a typical brain wave signal. This output signal is applied to input stage 36 via resistors R38 and R39, and is also applied to inverting amplifier A10 via switch 14c. Amplifier A10 and resistors R40-R42 function to invert the signal on line 52 and multiply the amplitude thereof by 2. Thus, by combining the output of amplifier A10 with the signal applied to the input of amplifier A2, amplifier A2 effectively receives a signal equal in amplitude but opposite in polarity to that on line 52. The effect of the signal produced by amplifier A10 on the input to amplifier A1 is substantially reduced by the additional resistor R39. Therefore, the signals applied to the inputs of amplifiers A1 and A2 are substantially of equal amplitude and opposite polarity. Since the signals on line 52 and from amplifier A10 are much greater in magnitude than any brain wave signals present at the input to stage 35, their effect on the system test is negligible. Finally, by closing switch 14b, low impedance (around 30 ohms) resistors R35a and R35b are added to the circuit to thereby reduce the amplitude of the signals applied to stage 35 to approximately 50 uV, a typical brain wave amplitude. By applying such signals of known amplitude, polarity and frequency to each of the Power Spectrum Analyzers 26 and 28, the power and frequency displays 10 and 12 should produce a predetermined indication. In the event that this indication is not so produced, the operator is immediately aware that the portion of the system is malfunctioning. Of course, control knob 4 which controls variable resistors R22 must be set to a predetermined position for the test.

Each of the linear LED arrays 10a, 10b, 12a and 12b may be comprised of the circuitry illustrated in FIG. 6. With reference to FIG. 6, an associated one of the signals to be displayed from Power Spectrum Analyzers 26 and 28 is applied to pin 5 of IC4 which is an LED driver such as the LM3914. Pins 6 and 7 are connected directly to each other, and are connected to pin 8 via resistor R58. Pin 8 is further applied to ground via variable resistor R57. Pins 4 and 2 are connected directly to ground, while pin 3 receives the supply voltage. Pins 1, and 18-10 from IC4 are applied to the cathodes of a linear array of diodes in display device 58, the positive supply voltage being applied to the anodes of the LED's.

IC4 operates to provide a path to ground for the cathodes of a number of the LEDs in display 58 to thereby illuminate the associated diodes, the number of diodes provided with the cathode path to ground being proportional to the voltage supplied to pin 5 of IC4.

Thus, a direct read-out of the amplitude of the output signals is provided as a "bar graph" type display.

The Table below lists approximate component values which have been successfully used in the brain wave monitoring device. These values are only used as examples for providing a working device and various alternatives to these values will be apparent to those skilled in the art.

While the preferred embodiments have been described with reference to the specification, the scope of the invention will be defined in accordance with the following claims.

TABLE

| Element No. | Resistors (ohms) | Capacitors (uf) | Amplifiers | IC's |
|---|---|---|---|---|
| 1 | 10M | .1 | LF 353 | LM2907 |
| 2 | 10M | .1 | LF 353 | CD4046 |
| 3 | 1K | 47 | LF 353 | LM555 |
| 4 | 1K | 47 | MC 1458 | LM3914 |
| 5 | 1M | 10 | LF 353 | |
| 6 | 1M | 10 | MC 1458 | |
| 7 | 1K | 10 | MC 1458 | |
| 8 | 1K | 10 | MC 1458 | |
| 9 | 27K | 10 | 741 | |
| 10 | 47K | 22 | 741 | |
| 11 | 1K | 10 | 741 | |
| 12 | 100K | .02 | 741 | |
| 13 | 1K | 1.5 | 741 | |
| 14 | 1K | 4.7 | 741 | |
| 15 | 1K | .002 | | |
| 16 | 27K | .02 | | |
| 17 | 47K | .1 | | |
| 18 | 10K | 1.5 | | |
| 19 | 10K | .1 | | |
| 20 | 15K | .1 | | |
| 21 | 100K | .1 | | |
| 22 | 10K | .1 | | |
| 23 | 4.7K | 10 | | |
| 24 | 1K | | | |
| 25 | 1M | | | |
| 26 | 10K | | | |
| 27 | 22K | | | |
| 28 | 33K | | | |
| 29 | 1K | | | |
| 30 | 220K | | | |
| 31 | 47K | | | |
| 32 | 27K | | | |
| 33 | 1M | | | |
| 34 | 4.7K | | | |
| 35a,b | 30 | | | |
| 36 | 100K | | | |
| 37 | 100K | | | |
| 38 | 100K | | | |
| 39 | 100K | | | |
| 40 | 1K | | | |
| 41 | 2.2K | | | |
| 42 | 1K | | | |
| 43 | 10K | | | |
| 44 | 10K | | | |
| 45 | 1M | | | |
| 46 | 1K | | | |
| 47 | 10K | | | |
| 48 | 10K | | | |
| 49 | 100K | | | |
| 50 | 500 | | | |
| 51 | 1M | | | |
| 52 | 1K | | | |
| 53 | 10K | | | |
| 54 | 10K | | | |
| 55 | 100K | | | |
| 56 | 500 | | | |
| 57 | 1K | | | |
| 58 | 270 | | | |

What is claimed is:

1. A device for monitoring brain wave activity during an operation on a patient, said activity detected by a pair of electrodes respectively placed on the left and right hemispheres of said patient's head, said device comprising:
   left and right analyzing means each receiving said brain waves from an associated one of said pair of electrodes, each of said left and right analyzing means providing brain wave amplitude and frequency information from said left and right hemispheres, respectively;
   a brain wave amplitude display having first and second linear indicator arrays disposed substantially side-by-side for receiving and displaying said brain wave amplitude information from said first and second hemispheres, respectively;
   a brain wave frequency display having first and second linear indicator arrays disposed substantially side-by-side for receiving said brain wave frequency information from said first and second hemispheres, respectively, and for displaying the instantaneous frequency of said brain waves from said first and second hemispheres of the brain on said respective first and second linear indicator arrays; and
   an audible brain wave amplitude indicator for selectively receiving said brain wave amplitude information from one of said left and right hemispheres via switch means, and having means for converting said brain wave amplitude information into an audio signal having a frequency proportional to the amplitude of said brain wave,
   whereby the combination of said brain wave amplitude display said brain wave frequency display, and said audible brain wave amplitude indicator facilitate the detection of general brain dysfunction and unilateral hemisphere dysfunction.

2. The device of claim 1 wherein each of said left and right analyzing means comprises filter means for receiving said brain waves and having a predetermined pass band, said filter means providing a filtered output;
   detector means receiving said filtered output for detecting the amplitude of said brain waves for providing said brain wave amplitude information in accordance with said detected amplitude; and
   converter means receiving said filtered output for detecting, over a frequency range greater than said predetermined pass band, the frequency of said brain waves having amplitudes above a predetermined amplitude, said converter means providing said brain wave frequency information in accordance with the detected frequency, to thereby allow the frequency of said brain wave to be tracked over said frequency range greater than said predetermined pass band.

3. A brain wave analyzer adapted to receive brain wave signals from a patient undergoing an operation, analyze said brain wave signals, and provide brain wave frequency and amplitude information, said brain wave analyzer comprising:
   filter means for receiving said brain wave signal and having a predetermined pass band, said filter means providing a filtered output;
   detector means for receiving said filtered output for detecting the amplitude of said brain wave signal and for providing said brain wave amplitude information in accordance with said detected amplitude;
   converter means for receiving said filtered output for detecting, over a frequency range greater than said predetermined pass band, the instantaneous frequency of said brain wave signals having amplitudes above a predetermined amplitude, and for providing said brain wave frequency information in accordance with said detected frequency, to thereby allow the frequency of said brain wave signal to be tracked over said frequency range greater than said pass band;

and linear amplitude and frequency displays for displaying said amplitude and frequency information.

4. The brain wave analyzer of claims 2 or 3 wherein said converter means includes selector means for selecting only those brain wave signals having amplitudes above said predetermined amplitude to provide selected signals, zero crossing detector means for receiving said selected signals for providing a zero crossing output upon the occurrence of a zero crossing of said selected signal, and frequency-to-voltage conversion means for receiving said zero crossing output for providing a voltage proportional to the frequency of said zero crossing output.

5. The brain wave analyzer of claim 4 wherein said selector means comprises a Schmidt trigger.

6. The brain wave analyzer of claim 5 wherein said detector means comprises a half-wave rectifier.

7. The brain wave analyzer of claim 6 wherein said filter means comprise at least one Butterworth filter.

* * * * *